United States Patent
Zhu et al.

(10) Patent No.: US 6,630,557 B2
(45) Date of Patent: Oct. 7, 2003

(54) TERTIARY AMINE METHACRYLATE-BASED MACROMONOMERS AND POLYMERS

(76) Inventors: Shiping Zhu, McMaster University, Department of Chemical Engineering, Hamilton, Ontario (CA), L8S 4L7; Youqing Shen, McMaster University, Department of Chemical Engineering, Hamilton, Ontario (CA), L8S 4L7; Robert Pelton, McMaster University, Department of Chemical Engineering, Hamilton, Ontario (CA), L8S 4L7

( * ) Notice: Subject to any disclaimer, the term of this patent is extended or adjusted under 35 U.S.C. 154(b) by 0 days.

(21) Appl. No.: 10/019,023

(22) PCT Filed: May 2, 2001

(86) PCT No.: PCT/CA01/00614
§ 371 (c)(1),
(2), (4) Date: Mar. 13, 2002

(87) PCT Pub. No.: WO01/83424
PCT Pub. Date: Nov. 8, 2001

(65) Prior Publication Data
US 2003/0078355 A1 Apr. 24, 2003

(30) Foreign Application Priority Data
May 3, 2000 (CA) ............................................... 2307438

(51) Int. Cl.$^7$ ............................................. C08F 120/24
(52) U.S. Cl. ...................... 526/311; 526/304; 526/306; 526/307.2; 526/319
(58) Field of Search ................................ 526/304, 306, 526/307.2, 311, 319

(56) References Cited
PUBLICATIONS

Lascelles et al., "Latex Syntheses Using Novel Tertiary Amine Methacrylate–Based Macromonomers Prepared by Oxyanionic Polymerization", *Macromolecules*, 1999, 2462–2471, 32.

Nagasaki et al., "A novel synthesis of semitelechelic functional poly(methacrylate)s through an ancoholate initiated polymeriztion. Syntheses of poly[2–(N,N–diethylaminoethyl) methacrylate] macromonomer", *Macromol. Rapid Commun.*, 1997, 827–835, 18.

Tokuda et al., "Cyclization of Aminyl Radicals Generated by Anodic Oxidation of Lithium Alkenylamides. Stereo– and Regioselective Synthesis of cis–1–ALKYL–2, 5–Disubstituted Pyrolidines", *Tetrahedron*, 1987, 281–296, 43:2, Great Britain.

*Primary Examiner*—Helen L. Pezzuto
(74) *Attorney, Agent, or Firm*—Jeffrey S. Melcher; Mandelli Denison & Selter, PLLC

(57) ABSTRACT

Compounds of general formula (I), the described methods to prepare these macromonomer compounds, and the copolymer products of these compounds with other vinyl monomers. Wherein W is a capping group; l is 0 or 1; n is 2–1000; m is 2–5; $R_1$ is $CH_2=CH-CH_2-$, or $CH_2=CH-O-R_8-$; $R_2$ is selected from H, $CH_2=CH-CH_2-$, and phenyl or alkyl and wherein $R_3-R_7$ is $H_1$, $C_1-C_4$ alkyl, and quaternary salts thereof. When R7 and X— is absent, the polymer is amphiphilic. When R7 is alkyl and X— is an anion, the polymer is cationic polymer.

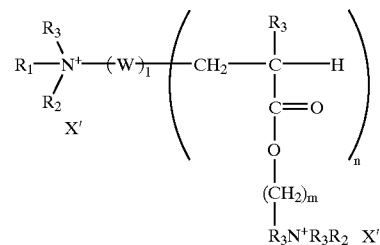

is 2-1000; m is 2-5.

20 Claims, 5 Drawing Sheets

TERTIARY AMINE METHACRYLATE-BASED MACROMONOMERS AND POLYMERS

FIELD OF THE INVENTION

This invention relates to tertiary amine methacrylate-based macromonomers and quaternary salts thereof; particularly macromonomers of dialkyl aminoethyl methacrylates with diallylalkylammonium or allylalkyl phenyl ammoniun or vinyloxypropyl terminal groups, polymers made therefrom and methods of preparation thereof.

BACKGROUND TO THE INVENTION

Random copolymers of cationic monomers with acrylamide are widely used to improve fines and filters retention during paper manufacture and sludge dewatering in newsprint deinking plants, as well as many other applications in mineral processing, oil recovery, and drinking water treatment.[1] Recently, it was demonstrated that graft copolymers, in which cationic units were concentrated on pendant chains, gave an much improved performance over their corresponding random polymers.[2,3] However, these graft copolymers were synthesized by a gamma radiation-initiated graft copolymerization. It was very difficult to control the copolymerization and almost impossible to completely analyze the copolymer structure. e.g. the length of grafted side chain and graft density. Copolymerization of acrylamide with cationic macromonomers provides a good approach to prepare such copolymers with required chain length and side chain density by controlling the chain length and charged amount of a macromonomer. Therefore the cationic macromonomer precursors need to be synthesized first.

Tertiary dialkylaminoethyl methacrylate based polymers can easily be converted to cationic polymers by quaternization of the tertiary amine. These cationic polymers are very useful in wastewater treatment and papermaking industries. Therefore, the synthesis of well-defined DMAEMA macromonomers with polymerizable terminal unsaturated group is of both industrial and academic interests.

Macromonomers with polymerizable vinyl terminal group are usually synthesized by end-group functionalization of pre-polymers and chain transfer radical polymerization catalyzed by cobalt compounds. Main problems for these methods are that usually not all of the end groups can be functionalized and the resulting polymers have broad molecular weight distribution.

The initiation method using vinyl-containing initiators is an effective alternative approach to the preparation of well-defined macromonomers with narrow molecular weight distributions. The advantage of this method is that each polymer chain has a terminal vinyl group. The application of the initiation method in the synthesis of poly(meth)acrylate macromonomers is still very limited because it is difficult for an initiator such as alkyllithium to bear an unsaturated group.[4] Recently, Nagasaki[5] and Lascelles[6] synthesized poly(diethylaminoethyl methacrylate) (polyDEAEMA) and poly(dimethylaminoethyl methacrylate) (polyDMAEMA) macromonomers with polymerizable terminal vinyl groups by using less active oxyanionic initiators. However, the molecular weights of the prepared polymers were higher than predicted and the polymer dispersities were about 1.3.

REFERENCES

1 Bolto, B. A. *Prog. Polym. Sci.* 1995, 20, 987
2 Ma, M., Zhu, S. *Colloid Polym. Sci.* 1999, 277, 123
3 Subramanian, R., Zhu, S., Pelton, R. H. *Colloid Polym. Sci.* 1999 to appear.
4 Jerome, R., Teyssie, Ph., Vuillemin, B., Zundel, T., Zune, C. *J. Polym. Sci. Polym. Chem.* 1999, 37, 1
5 Nagasaki, Y., Sato, Y., Kato, M. *Macromol. Rapid Commun.* 1997, 18, 827
6 Lascelles, S. F., Malet, F., Mayada, R., Billingham, N.C., Armes, S. P. *Macromolecules.* 1999, 32, 2462

SUMMARY OF THE INVENTION

The invention in one aspect provides compounds of the general formula I wherein W is a capping group; l is or 1; n is 1–1000; m is 1–5; preferably m is 2;

$R_1$ is selected from $CH_2=CH—CH_2—$ and $CH_2=CH—O—(CH_2)_p—$; p is 1–5;

$R_2$ is selected from H, $CH_2=CH—CH_2—$, and phenyl and wherein $R_3$–$R_5$ is $C_1$–$C_4$ alkyl, and quaternary salts thereof wherein $R_6$ is $C_1$–$C_4$ alkyl and $X^-$ is an anion.

Preferably, m is 2 when $R_3$ is $CH_3$.

When amphiphilic macromonomers are needed, $R_4$–$R_5$ are $C_1$–$C_4$ alkyls and $R_6$ is absent to thus represent non-quaternized macropolymers.

When cationic macromonomers are desired, $R_4$–$R_6$ are $C_1$–$C_4$ alkyls, and complementary X are present.

Most preferably, n is selected from 5–200 and, still further preferred, n is 10–100.

Water-soluble cationic macromonomers of dialkylaminoalkyl methacrylate with polymerizable diallylmethylammonium or allylmethylphenylammonium or vinyloxyalkyl terminal groups embodiments of the aforesaid compounds according to the invention were synthesized by N-substituted amine—butyllithium (BuLi) initiated anionic polymerization of dialkylaminoalkyl methaerylate, particularly, DMAEMA and subsequent quaternization. We found that diallylamine-BuLi initiated a living polymerization. The resulting polymers had a very narrow molecular weight distribution with initiator efficiency about 0.25. The initiator efficiency of allylphenylamine-BuLi was as high as 0.63. A capping method was thus developed to improve the initiator efficiency of dilallylamine-sBuLi system. Capped with dimethylacrylamide (DMA) or tert-butyl methacrylate (tBMA), the initiation efficiency of the diallylamine-sBuLi system was increased to a level as high as 0–95. Similarly, DMA-capped vinyloxypropylamine-sBuLi had about 0.6 initiator efficiency, but its uncapped system could not initiate the polymerization. The polymerization produced amphiphilic macromonomers with predictable molecular weight and extremely low polydispersity. The quaternization of the polymers with $CH_3I$ and dimethyl sulfate gave corresponding cationic macromonomers with diallylmethylammonium or allylmethylphenylammonium, or vinyloxypropyl end groups, which were readily polymerizable by free radical polymerization mechanism.

Thus, in one aspect of the invention provides the synthesis and characterization of cationic macromonomers with diallylmethylammonium or allylmethylphenyl ammonium or vinyloxypropyl terminal group by a living polymerization of DMAEMA. These vinyl groups are active double bonds for the copolymerization with water-soluble monomers such as acrylamide or other organic soluble monomers such as methymethacrylate (MMA) and styrene (St) to make amphiphillic copolymers Scheme 1. Synthesis of DMAEMA cationic macronomer by living anionic polymerization of DMEAMA.

Diallylamine: $R_1=R_2=$allyl; $CH_2=CH-CH_2$

Allylaniline: $R_1=$allyl, $R_2=$phenyl

Thus, the present invention in one aspect provides poly-DMAEMA macromonomers with polymerizable terminal vinyl groups synthesized by a living anionic polymerization with N-substituted amine-butyllithium initiator system. We have found that the alkylamine substituent had a strong effect on the initiator efficiency in the order of H<allyl<phenyl. We have found that the capping of diallylaminolithium with dimethylacrylamide or t-butylmethacrylate gave high initiator efficiencies and an excellent control of the molecular weight. Still further, we have also found that a one to three-fold LiCl with respect to the initiator gave polyDMAEMA with controlled molecular weight and narrow molecular weight distribution. However, too excess LiCl reduced the initiator efficiency. We have also found that the quaternization of terminal diallylamino and allylphenylamino groups required a strong methylizating agent such as $(CH_3)_2SO_4$, while the dimethylamino group in the polymer chain was quaternized by $CH_3I$.

We have found that lithium amides prepared from primary amine-BuLi could not initiate the polymerization of DMAEMA. However, when these lithium amides were capped with dimethylacrylamide (DMA), named as capping agent, they could initiated the DMAEMA polymerization and yielded polymers with narrow molecular weight distribution. Thus the invention also provides the synthesis of amphiphilic and cationic macromonomers of DMAEMA with the terminal vinyl or allyl group by the living DMAEMA polymerization initiated by capped primary amine-BuLi systems. Further, we have found that vinyl-terminated poly(DMAEMA) and its corresponding cationic macromonomers or diallylmethylammonium terminated cationic macromonomers are readily copolymerizable with other vinyl monomers such as styrene and acrylamide, while allyl-terminated macromonomers are versatile for further modification, for example, hydrosillation, transformation with epoxy and hydroxyl groups, and synthesis of block and graft copolymers.

BRIEF DESCRIPTION OF THE DRAWINGS

In order that the invention may be better understood preferred embodiments will now be described by way of example only, with reference to the accompanying drawings wherein:—

DETAILED DESCRIPTION OF PREFERRED EMBODIMENTS

Experimental Section
Reagents and Solvents

Dimethylaminoethyl methacrylate (DMAEMA) from Aldrich was stirred over $CaH_2$ for 24 h, then was distilled from $CaH_2$ under a reduced pressure and stored under nitrogen in a refrigerator. LiCl (99.9%) from Aldrich was dried at 130° C. and then dried again at 100° C. under vacuum just before use. THF was refluxed over potassium under nitrogen atmosphere. Diallylamine, allylamine and allylaniline were distilled over $CaH_2$. Secondary-butyllithium (sBuLi) was purchased from Aldrich and its concentration was titrated by a standard method. 3-Aminopropyl vinyl ether (AVE) (Aldrich), aminostyrene (AS) (Alfa Aser) and allylamine (AA) (Aldrich) were dried and distilled over $CaH_2$.

Preparation of Initiator and Polymerization

In a glass reactor previously treated with chlorotrimethylsilane and flame dried, weighted LiCl was added and heated to 100° C. under vacuum and purged with nitrogen 5 times. Then 30 ml THF and required amount of N-substituted allylamine were charged to the reactor. The reactor was cooled down to −78° C. A stoichiometric amount of s-butyllithium was added dropwisely with stirring. After 1 h of stirring, the monomer was introduced. In the runs with a capping agent, 2-fold (molar) dimethylacrylamide or tert-butyl methacrylate with respect to N-substituted allylamine was introduced and stirred at −78° C. for 0.5 h before adding monomer. The polymerization was terminated by adding 0.2 ml methanol. The aliquot was then poured into 200-ml petroleum ether. Finally the polymer was separated and dried in vacuum at 30° C. for 24 h.

ization were summarized in Table 1. If both the initiator preparation and polymerization of DMAEMA were carried out at 0° C., the polymerization gave only 33% polymer (Table 1, entry 1). If the initiator was prepared at 0 or 25° C. while the polymerization was carried out at −78° C., the conversion was almost complete, but the molecular weight of the resulted polymer deviated far from the predicted (Table 1, entries 2 and 3). The initiation efficiency (the ratio of calculated Mn over measured Mn) with respect to diallylamine was about 15% only.

TABLE 1

Synthesis of PDMAEMA macromonomers by living polymerization of DMAEMA initiated by alkylamine/s-butyllithium in the presence of Lithium chloride

| Run | Init. | Reaction Temp. (° C.) | Polym. Temp. (° C.) | LiCl/ BuLi | DA/ BuLi | Conv. (%) | Calculated DP | Mn (GPC) | Efficiency | Mw/Mn |
|---|---|---|---|---|---|---|---|---|---|---|
| 1 | DA | 0 | 0 | 10 | 1 | 33 | 1884 | 3500 | — | 1.11 |
| 2 | DA | 25 | −78 | 10 | 1 | 99 | 4700 | 32700 | 0.16 | 1.09 |
| 3 | DA | 0 | −78 | 10 | 1 | 98 | 4700 | 29000 | 0.14 | 1.10 |
| 4 | DA | −78 | −78 | 0 | 1 | 99 | 4700 | 17200 | 0.27 | 2.49 |
| 5 | DA | −78 | −78 | 1 | 1 | 99 | 4700 | 19000 | 0.24 | 1.07 |
| 6 | DA | −78 | −78 | 3 | 1 | 98 | 4700 | 18800 | 0.25 | 1.08 |
| 7 | DA | −78 | −78 | 10 | 1 | 99 | 4700 | 19000 | 0.24 | 1.05 |
| 8 | DA | −78 | −78 | 1 | 10 | 98 | 4700 | 19600 | 0.24 | 1.04 |
| 9 | DA | −78 | −78 | 10 | 10 | 97 | 9600 | 24600 | 0.39 | 1.02 |
| 10 | DA | −78 | −78 | 10 | 10 | 97 | 12700 | 36600 | 0.35 | 1.02 |
| 11 | AAM | −78 | −78 | 10 | 10 | 98 | 5024 | 8000 | 0.63 | 1.11 |
| 12 | AAn | −78 | −78 | 10 | 10 | 0 | — | — | — | — |

[alkylaminolithium] = 0.017 mol/L; DA = diallylamine; AAM = allylamine; AAn = allylaniline Quaternization of the Polymers 1 g polymer was dissolved in 10 ml acetone or DMSO or dimethylforamide (DMF) at room temperature. 0.5 ml $CH_3I$ was then added dropwisely and stirred for 2 h. 0.1 ml dimethyl sulfate was then added and the solution was stirred for another hour. When using acetone as solvent, the quaternized polymer precipitated very quickly after adding $CH_3I$. The precipitate was isolated and dried in the vacuum oven. When DMSO or DMF was used as solvent, the quaternized polymer was soluble in DMSO and therefore the reaction in DMSO or DMF was homogenous The quaternized polymer was precipitated in acetone and also dried in vacuum.

Characterization

Nuclear Magnetic Resonance (NMR) Spectroscopy: Proton ($^1H$) NMR spectra were recorded on a Bruker ARX-200 spectrometer at 200 MHz. $^1H$ NMR chemical shifts in $CDCl_3$ were reported downfield from 0.00 ppm using $CHCl_3$ signal at 7.23 ppm as an internal reference. When $D_2O$ was used as solvent, $H_2O$ signal at 4.63 ppm was used as reference.

Molecular Weight Measurements: Number and weight average molecular weights ($M_n$ and $M_w$, respectively) were determined by gel permeation chromatography (GPC) using THF-2% (v/v) trimethylamine as eluent at 25° C. with RI detector. Narrow polystyrene standards (Polysciences) were used to generate a calibration curve (Varian MicroPak column G1000, 3000, 7000 HXL). Data were recorded and processed using the Windows based Millenium 2.0 software package.

Results

Figure 1:
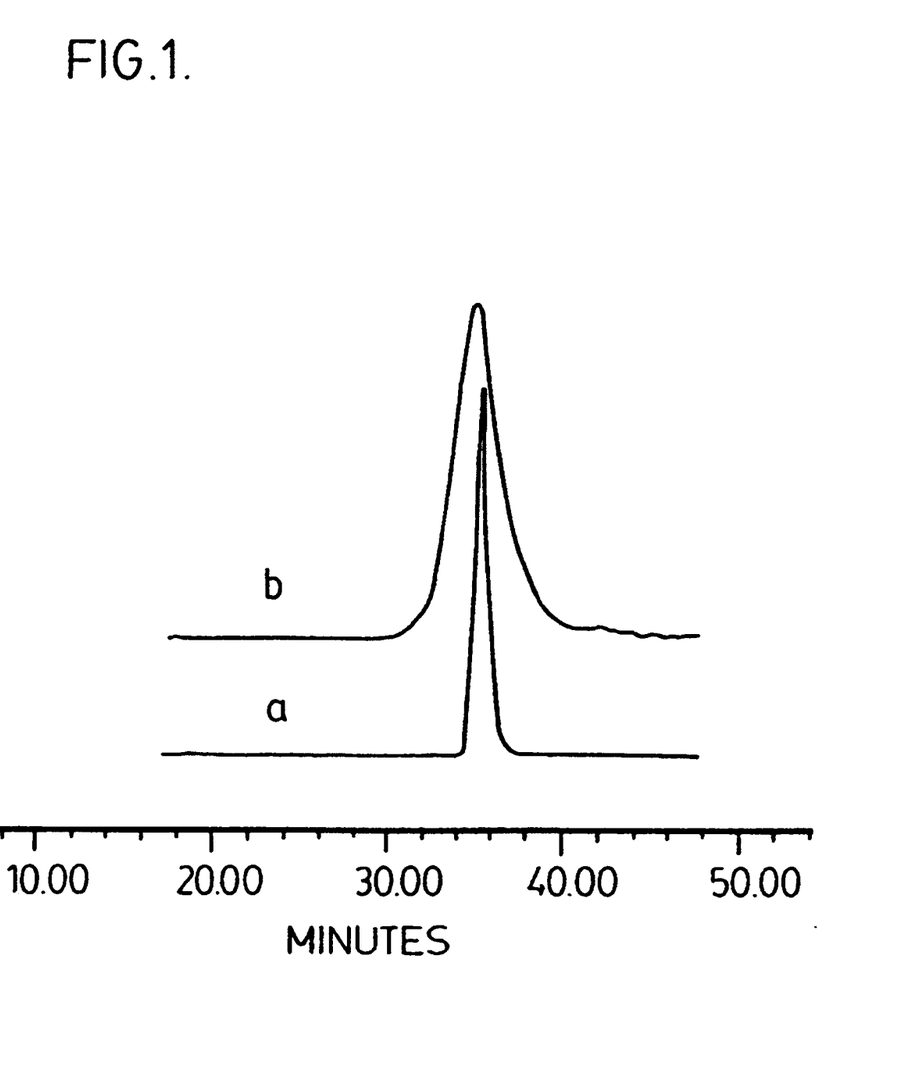
FIG. 1 is a gel permeation chromatography (GPC) scan showing GPC traces of polyDMAEMA initiated by diallylamine-sBuLi: (a) Table 1 entry 6 and (b) Table 1 entry 4.

1. DMAEMA Polymerization by N-Substituted Allylamine-sBuLi Initiator System The initiator, N-substituted allylaninolithium, was prepared in-situ by the reaction of N-substituted allylamine with s-butyllithium (see Scheme 1). The effects of experimental conditions for the initiator preparation and polymer- When both the initiator preparation and successive polymerization were carried out at −78° C., the initiator efficiency increased to about 25% as shown in Table 1. The corresponding GPC trace (FIG. 1, a) shows a unimodal with extremely narrow molecular weight distribution. This result indicates that the initiation reaction was very fast and that once a polymer chain started to propagate, there was no side reaction of the polymer anion. Furthermore, the amount of added LiCl had some effect on the polymerization. In the absence of LiCl, the polymerization produced polymer with very broad molecular weight distribution (Mw/Mn=2.49) (FIG. 1b). But in the presence of LiCl, the polymer appeared to be nearly monodispersed (Table 1, entries 5–7) (FIG. 1a). It seems that the presence of LiCl suppressed side reactions of the living polymeric carbanion attacking the carbonyl groups in the polymer and monomer.[4] However, the presence of LiCl did not increase the initiation efficiency. With or without LiCl, the initiation efficiencies of diallylamine were about 0.25.

The effect of added amount of diallylamine was also investigated. Interestingly, the presence of excessive diallylamine did not decrease the molecular weight of polyDMAEMA, as shown in Table 1 entry 8. Given the same concentration of s-butyllithium (compared to entry 5), the molecular weight of polyDMAEMA remained unchanged and the molecular weight distribution of prepared polyDMAEMA was still narrow, regardless of the amount of added diallylamine. This indicates that the formed carbanions did not abstract the N—H hydrogen on diallylamine (Scheme 2). Thus, sBuLi can be allowed to react with an excess amount of diallylamine to minimize side reactions of sBuLi during the initiator preparation.

Scheme 2. No chain transfer of polymer anion to diallylamine

Allylaniline (AAn) and allylamine (AAm) were also tested for the polymerization of DMAEMA to further investigate the effect of alkyl moiety on the initiator efficiency (Table 1, entries 11 and 12). When allylaninolithium (Scheme 3b), prepared by the reaction of allylamine with sBuLi, was used as initiator, no polymer was obtained, while allylphenylaminolithium (Scheme 3c), derived from the reaction of allylaniline with sBuLi, had much higher initiator efficiency, 0.63, than that of diallylaminolithium (Scheme 3a). Apparently, the structure of the nitrogen substituent influences the initiator efficiency. For N-substututed allylamines, the efficiency increased in the order of H<<allyl<phenyl.

Scheme 3. Schematic structures of N-substituted allylaminolithium

2. Diallylamine/sBuLi-Capping Agent Initiated Polymerization of DMAEMA

In an effort to improve initiator efficiency, the diallylaminolithium was capped with dimethylacrylamide (DMA) and tert-butyl methacrylate (tBMA) and the polymerization results were summarized in Table 2.

Scheme 4. Capping reaction of diallylaminolithium with DMA and tBMA

TABLE 2

DMAEMA polymerization initiated by capped-diallylaminolithium at −78° C.[a]

| Run | Caaping agent | DMAEMA/ LiCl ratio | Solvent | Solvent | Conv. (%) | Mn Calcu. | Mn GPC | Initiator Efficiency | Mw/Mn |
|---|---|---|---|---|---|---|---|---|---|
| 1 | DMA | 30 | 0 | THF | 99 | 4700 | 38300 | 0.12 | 2.89 |
| 2 | DMA | 30 | 1 | THF | 98 | 4700 | 5310 | 0.89 | 1.06 |
| 3 | DMA | 27 | 3 | THF | 99 | 4200 | 4440 | 0.95 | 1.04 |
| 4 | DMA | 40 | 3 | THF | 99 | 6280 | 6500 | 0.96 | 1.08 |
| 5 | DMA | 78 | 3 | THF | 98 | 12300 | 13700 | 0.90 | 1.08 |
| 6 | DMA | 150 | 3 | THF | 99 | 23300 | 25500 | 0.93 | 1.04 |
| 7 | DMA | 30 | 3 | THF-Toluene[b] | 95 | 4700 | 24600 | 0.19 | 4.86 |
| 8 | DMA | 30 | 10 | THF | 99 | 4700 | 9600 | 0.49 | 1.06 |
| 9 | DMA | 60 | 10 | THF | 100 | 9420 | 15000 | 0.63 | 1.08 |
| 10 | tBMA | 30 | 3 | THF | 99 | 4700 | 4900 | 0.96 | 1.03 |
| 11 | tBMA | 50 | 3 | THF | 99 | 7800 | 8300 | 0.94 | 1.05 |

TABLE 2-continued

DMAEMA polymerization initiated by capped-diallylaminolithium at −78° C.[a]

| Run | Caaping agent | DMAEMA/ LiCl ratio | Solvent | Solvent | Conv. (%) | Mn Calcu. | Mn GPC | Initiator Efficiency | Mw/Mn |
|---|---|---|---|---|---|---|---|---|---|
| 12 | tBMA | 64 | 3 | THF | 99 | 10000 | 11500 | 0.87 | 1.07 |
| 13 | tBMA | 60 | 10 | THF | 97 | 9420 | 17000 | 0.55 | 1.04 |
| 14 | MAN | 30 | 3 | THF | 100 | 4700 | 19500 | 0.21 | 1.31 |

[a][Diallylaminolithium] = 0.017 mol/L, [b]Toluene/THF = 9/1 (v/v).

The results in Table 2 show that DMA or tBMA-capped diallylaminolithium had very high activities. The monomer conversions were almost complete. More importantly, the molecular weights of the obtained polymers agreed with the calculated ones and the initiator efficiencies were as high as 0.95 in the presence of 3-fold LiCl (Table 2, entries 26, 10–12). The molecular weight distributions were very narrow with dispersities below 1.1. These results suggest that there were essentially no chain transfer and termination reactions. This assured that each polymer chain had one initiator terminal group, which is very important for the macromonomer.

Figure 2:
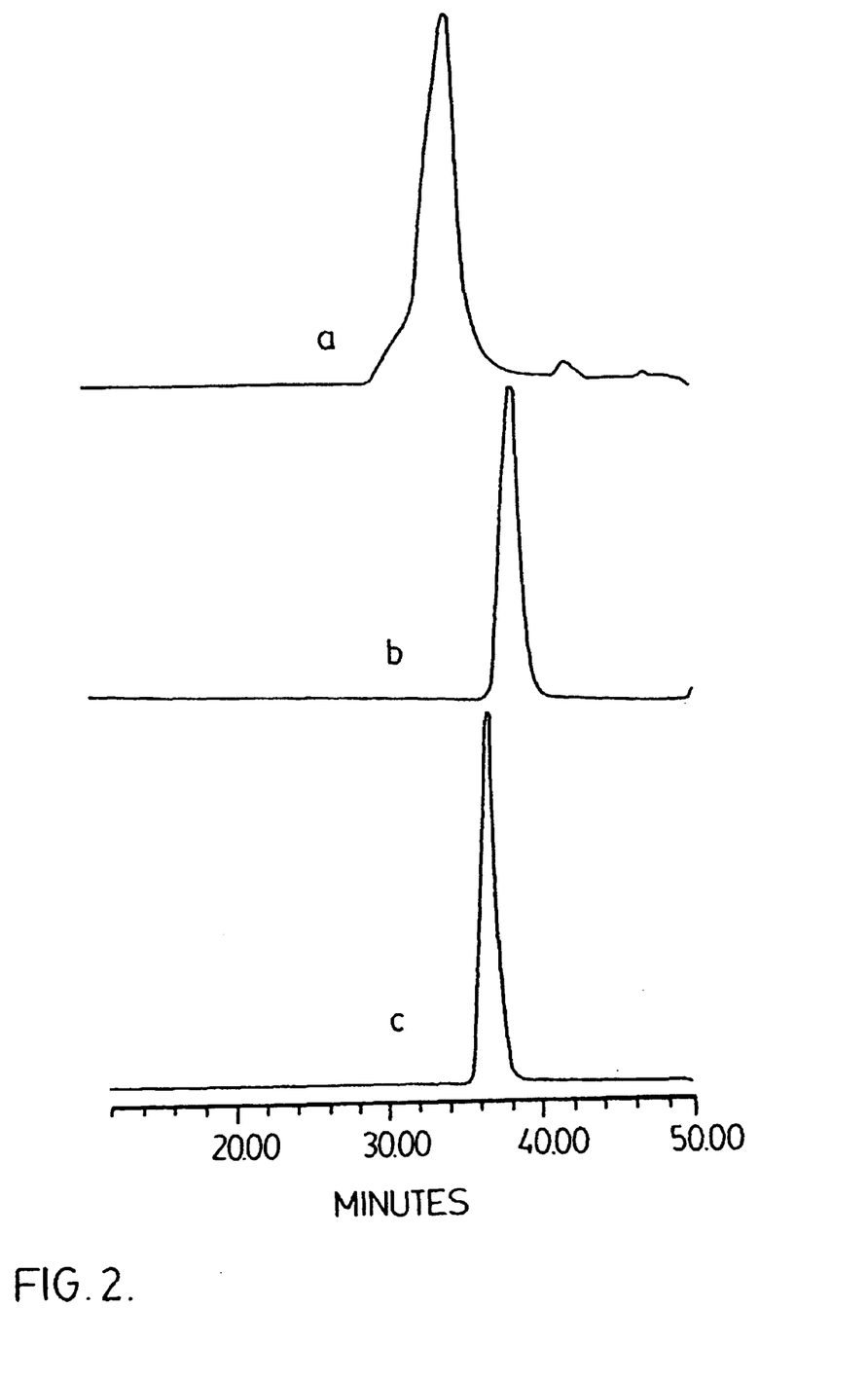
FIG. 2 is a GPC scan showing GPC traces of polyDMAEMA initiated by DMA-capped diallylaminolithium: (a) without LiCl (Table 2 entry 1), (b) with 3-fold LiCl (Table 2 entry 3), and (c) with 10-fold LiCl (Fable 2 entry 8)

The high efficiencies of the capped diallylaminolithium indicated a complete capping reaction. The narrow GPC traces of the resulting polymers (FIGS. 2b, c) demonstrated that there was only a single type of initiation center. It can be postulated that either diallylaminolithium did not strongly associate or it disassociated into monomeric structure in the presence of LiCl. This conclusion was confirmed by the diallyaminolithium-initiated homopolymerization of tBMA, in which high initiator efficiencies were also obtained. The low efficiency in the diallylaminolithium-initiated polymerization of DMAEMA was attributed to the reaction of diallyaminolithium with the monomer carbonyl group.

The LiCl amount in the polymerization system had a dramatic effect of the DMAEMA polymerization initiated by the capped diallylaminolithium. Without LiCl, DMA-capped diallylaminolithium had a very low initiation efficiency (Table 2 entry 1), and the polymer had a broad molecular weight distribution (FIG. 2a). However, adding 1 or 3-fold LiCl substantially increased the initiator efficiency up to 0.95 and yielded polymers with extremely narrow molecular weight distributions (Table 2 entries 2–6) (FIG. 2b). By contrast, the presence of LiCl did not improve the initiator efficiency of the uncapped diallylaminolithium (Table 1).

Very high LiCl addition had a detrimental effect on the initiation efficiency for both DMA and tBMA-capped diallylaminolithium (Table 2, entries 8, 9, 13). For example, the efficiencies of the capped diallylamino lithium decreased to about 0.5 with a 10-fold LiCl. This effect of excess LiCl may be due to the fact that there are too many LiCl molecules surrounding an initiator anion. Some initiators thus become dormant in clusters and inactive in the initiation of DMAEMA. We also tested toluene/THF (9:1 v/v) as a solvent and found low initiator efficiency and very poor control of molecular weight (Table 2 entry 7).

3. The DMAEAM Polymerization with Primary Amine-sBuLi System

As stated above, the primary amine-sBuLi without capping could not initiate DMAEMA polymerization. Table 3 also shows that the three primary amine-BuLi systems, AVE-BuLi, AS-BuLi and AA-BuLi, (Table 1, entries 1–3) could not initiate the DMAEMA polymerization.

TABLE 3

Synthesis of PDMAEMA macromonomers by living polymerization of DMAEMA initiated by primary amine-butyllithium in the presence of Lithium chloride.

| Run | Alkylamine | Cap agent | LiCl/BuLi | Conv. (%) | Mn (Calculated) | Mn (GPC) | I. E. | Mw/Mn |
|---|---|---|---|---|---|---|---|---|
| 1 | AVE | — | 3 | 0 | — | — | 0 | — |
| 2 | SA | — | 3 | 0 | — | — | 0 | — |
| 3 | AA | — | 3 | 0 | — | — | 0 | — |
| 4 | AVE | tBMA | 3 | 99 | 4900 | 25500 | 0.19 | 1.23 |
| 5 | AVE | DMA | 3 | 98 | 2555 | 4700 | 0.54 | 1.14 |
| 6 | AVE | DMA | 3 | 98 | 4900 | 8600 | 0.57 | 1.11 |
| 7 | AVE | DMA | 3 | 99 | 5200 | 9300 | 0.56 | 1.10 |
| 8 | AVE | DMA | 3 | 98 | 9620 | 16800 | 0.57 | 1.12 |
| 9 | AVE | DMA | 0 | 100 | 4900 | 39200 | 0.13 | 2.75 |
| 10 | AVE | DMA | 10 | 95 | 4900 | 15013 | 0.33 | 1.14 |
| 11 | AVE | DMA | 10 | 97 | 4900 | 11000 | 0.44 | 1.13 |
| 12 | AVE | DMA | 10 | 96 | 9620 | 25300 | 0.38 | 1.09 |
| 13 | AA | DMA | 3 | 99 | 2800 | 4750 | 0.59 | 1.09 |
| 14 | AA | DMA | 3 | 99 | 4900 | 8000 | 0.61 | 1.13 |
| 15 | AA | DMA | 3 | 100 | 6480 | 10550 | 0.61 | 1.08 |
| 16 | SA −78° C. in THF | DMA | 3 | 99 | 4900 | 17100 | 0.28 | 1.23 |

When tBMA was used as a capping agent, the capped AVE-BuLi could initiate the DMAEMA polymerization with near 100% conversion. However, the molecular weight of the resulted polymers was much higher than the predicated. The initiation efficiency of the tBMA-capped AVE-BuLi was only as low as 0.19. This was much lower than tBMA-capped diallylamine-BuLi system (initiator efficiency about 0.95) for the DMAEMA polymerization. By contrast, after being capped with DMA, AVE-BuLi and AA-BuLi initiator systems initiated a living polymerization of DMAEMA, yielding polymers with controlled molecular weight and low polydispersity, around 1.1. The molecular weights measured by GPC were about the half of the predicated. The initiator efficiencies of the capped AVE-BuLi and AA-BuLi systems were about 0.55.

4. Characterization of the Macromonomers

Figure 3:
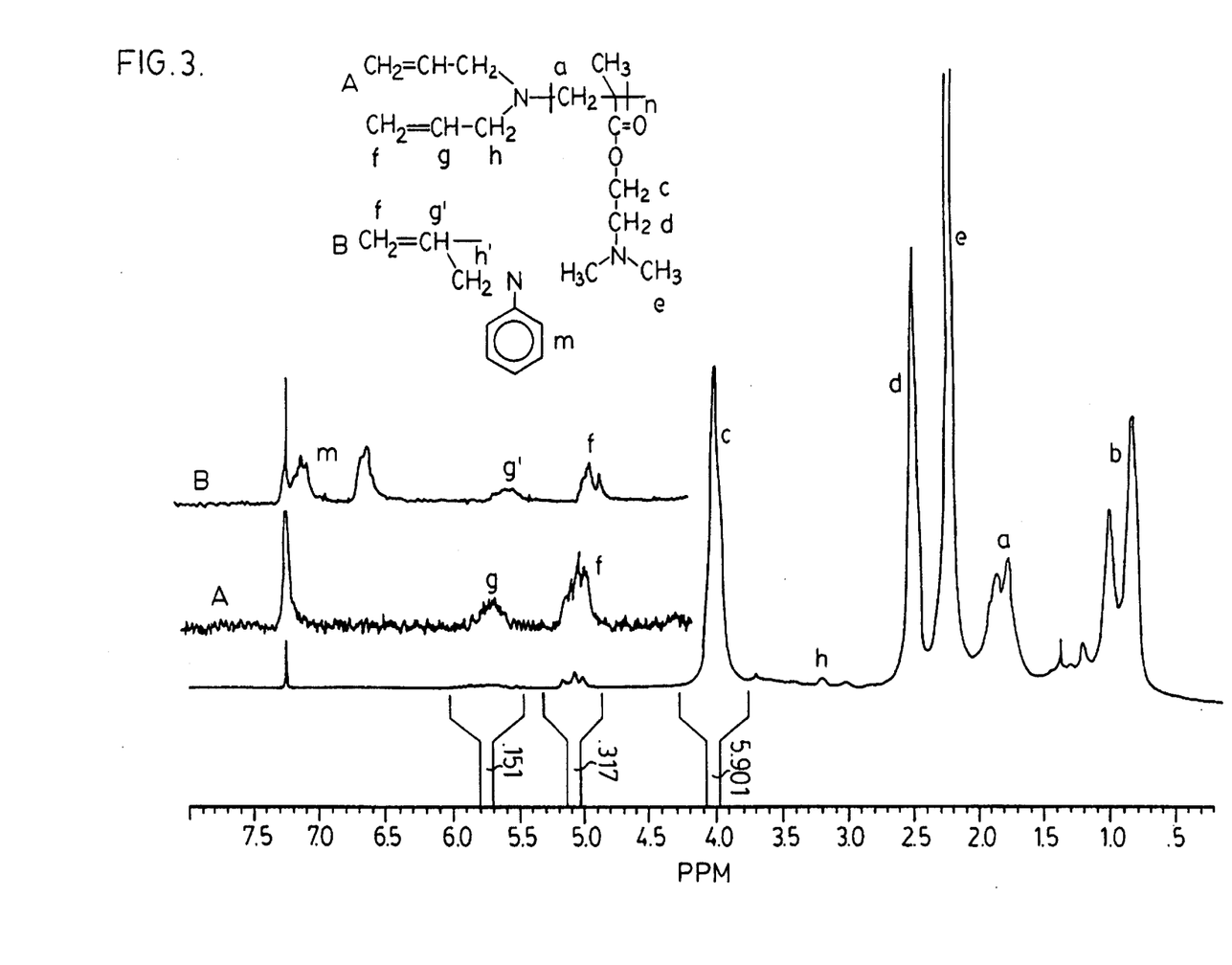
FIG. 3 is a nuclear magnetic resonance (NMR) scan showing $^1$H-NMR spectra of polyDMAEMA macromonomers prepared by (a) diallylamine-sBuLi and (b) allylphenylamine-sBuLi.

The macromonomers were characterized by $^1$H-NMR. FIG. 3 shows the NMR spectrum of polyDMAEMA prepared by diallylamine-sBuLi. Signals of polyDMAEMA backbone are 2.25 ppm (N(C$\underline{H}_3$)$_2$), 2.55 (NC$\underline{H}_2$), 4.05 ppm (COOC$\underline{H}_2$), 1.65~2.05 ppm (C$\underline{H}_2$—C—CH$_3$), 0.87 and 1.05 ppm (C$\underline{H}_3$—C). The double bond signals for diallylamino group appear at 5.1 ppm (multiple) (CH$_2$=) and 5.7 ppm (multiple) (=CH) (FIG. 3a), which are very similar to the signals of diallylamine. The signals of allyl group in allylphenylamino appear at up-field, 5.6 ppm (multiple) (=CH) and 5.05 ppm (multiple) (CH$_2$=), due to the conjugation of benzene ring with the nitrogen atom.

Figure 4:
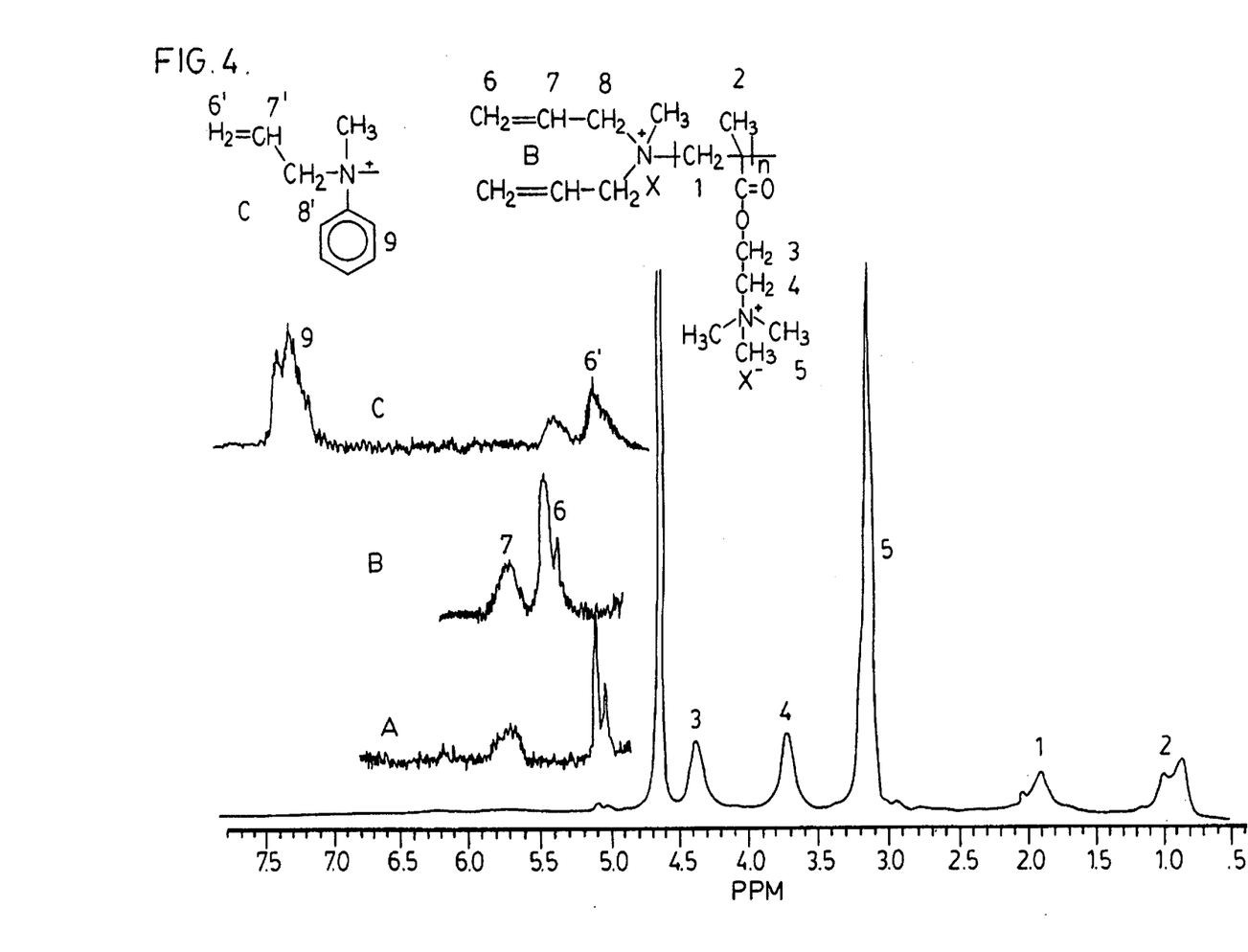
FIG. 4 is a NMR scan showing $^1$H-NMR spectra of quaternized polyDMAEMA macromonomers: (a) diallylamino-terminated polyDMAEMA reacted with $CH_3I$ at room temperature for 1 h, (b) diallylamino-terminated polyDMAEMA reacted with $(CH_3)_2SO_4$ in DMSO for 1 h, (c) allylphenylamino-terminated polyDMAEMA reacted with $(CH_3)_2SO_4$ in DMSO for 6 h.

The obtained polymers were reacted with quaternization agents to prepare polymerizable cationic macromonomers. Two types of tertiary amino groups—pendant dimethylamino and terminal diallyamino or allylphenylammino group—need to be quaternized. The terminal diallylamino ((CH$_2$=CH—CH$_2$)$_2$N—) or allylphenylamino ((CH$_2$=CH—CH$_2$N(C$_6$H$_5$)) group must be quaternized to make it polymerizable by free radical mechanism because un-quaternized diallylamine does not polymerize.[22] It was found that these two types of amino groups had very different reactivities. The dimethylamino group is very easy to be quaternized by CH$_3$I at room temperature or by benzyl chloride at 40° C. For example, after 1 h reaction with CH$_3$I at room temperature, all the dimethylamino groups were converted into trimethylammonium ((CH$_3$)$_3$N$^+$), as shown in FIG. 4. The signal for NC$\underline{H}_3$ at 2.25 ppm disappeared completely while a strong peak for N$^+$CH$_3$ appeared at 3.20 ppm.

Figure 5:
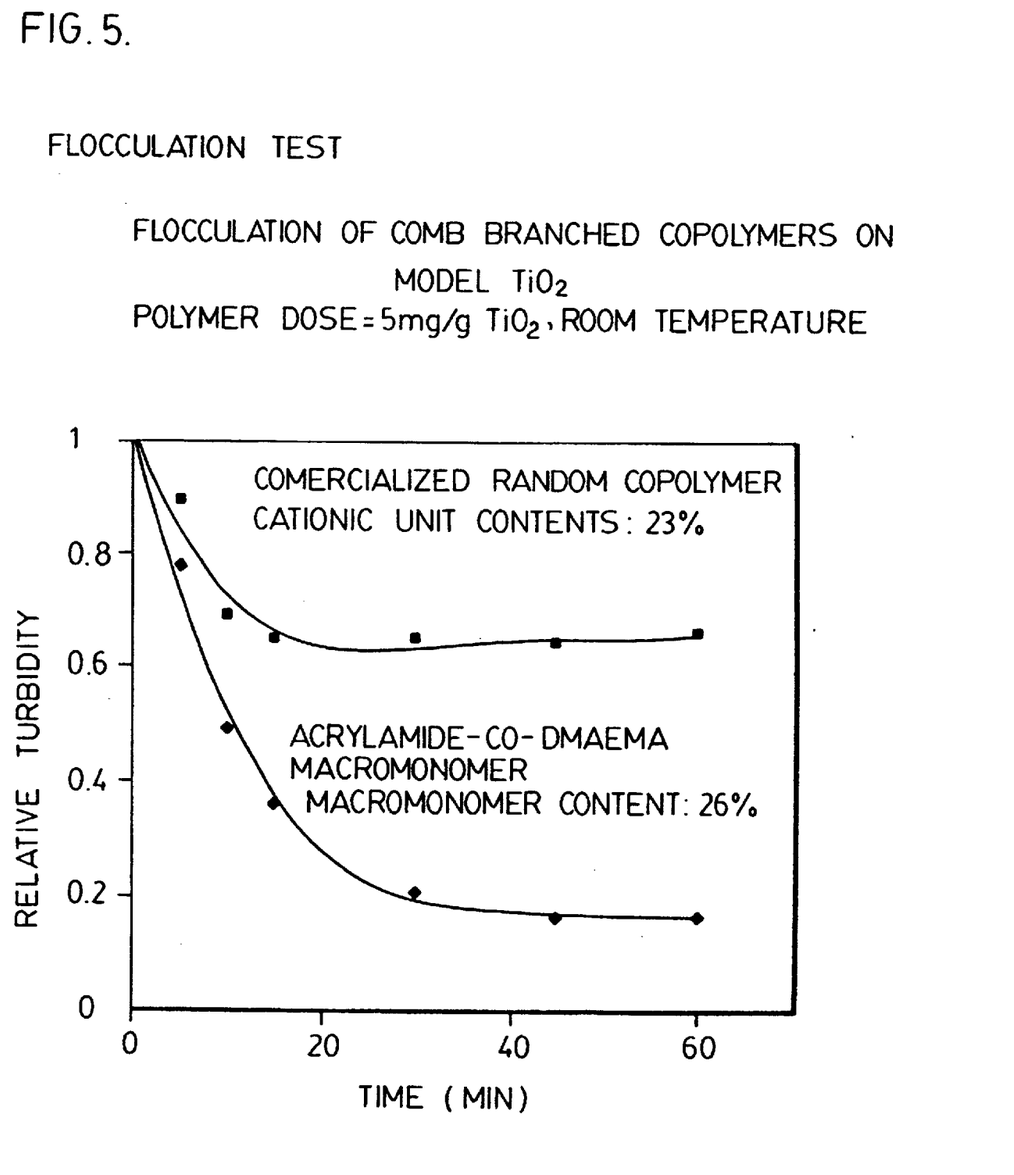
FIG. 5 represents a flocculation test graph showing relative turbidity against time.

However, there was no change for the allyl peak form either diallylamino or allylphenylamino terminal group (FIG. 5a). Increasing the quaternization temperature or prolonging the reaction time of CH$_3$I or PhCH$_2$Cl could only partially quaternize these terminal groups. Unfortunately those more extreme conditions caused some double bonds disappear, which was possibly due to reaction with I$_2$ generated from the decomposition of CH$_3$I.

The more powerful methylizating agent, (CH$_3$)$_2$SO$_4$, quantitatively quaternized both types of tertiary amino groups in the polymer. For example, after 1 h reaction in DMSO at room temperature, the terminal diallylamino group was completely quaternized, as seen in NMR spectra (FIG. 4b). The allyl proton signals at 5.1 ppm (CH$_2$=) and 5.7 ppm (=CH) shifted to 5.45 ppm and 5.70 ppm, respectively. The complete quaternization of allylphenylamino group with dimethyl sulfate required 6 h (FIG. 4c). This lower reactivity of allylphenylamino group may be due to the combination of high steric hindrance effect of the benzene ring and the conjugation of the nitrogen atom with benzene ring, which substantially decreases the electron density on the nitrogen atom.

5. Copolymerization with Acrylamide

Copolymerization of the quaternized macromonomer with acrylamide was conducted using AIBA as a radical initiator. 1 g (M$_n$=9000) of the macromonomer, 1 g of acrylamide, 5 mg of AIBA and 15 mL of water were charged to a tube reactor. The tube was degassed with argon for ten minutes and sealed with rubber septum. The tube was then immersed into a water bath at 60° C. After reaction for 4 h, the polymer was precipitated in methanol and dried in vacuum to yield 1.8 g of comb polymer with conversion 90% with respect to the total monomers charged.

FIG. 5 shows the improved flocculation properties of a comb-branched copolymer on a TiO$_2$ particulate aqueous suspension.

The acrylamide-co-DMAEMA macromonomer had a macromonomer content of 26% (A) and prior art random copolymer cationic unit content of 23%.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

What is claimed is:

1. Compounds of the general formula I wherein W is a capping group; l is 0 or 1; n is 1–1000; m is 1–5; R$_1$ is selected from CH$_2$=CH—CH$_2$— and CH$_2$=CH—O—(CH$_2$)$_p$—, p is 1–5; R$_2$ is selected from H, C$_1$-C$_4$alkyl, CH$_2$=CH—CH$_2$—, or phenyl; when R$_1$ is CH$_2$=CH—O—(CH$_2$)$_p$, R$_2$ is H or C$_1$-C$_4$alkyl; and R$_3$-R$_6$ are C$_1$-C$_4$ alkyl; and quaternary salts thereof when R$_6$ is C$_1$-C$_4$alkyl and X is an anion.

2. Compound as defined in claim 1 wherein m is 2 and R$_3$-R$_6$ is C$_1$-C$_4$ alkyl.

3. Compound as defined in claim 1 wherein m is 2 and R$_3$ is CH$_3$.

4. Compound of claim 1 wherein n is 5–200.

5. Compound of claim 1 wherein n is 10–100.

6. Compound of claim 1 wherein R$_6$ is CH$_3$.

7. Compound as defined in any one of claims 1 to 6 wherein W is selected from wherein R$_7$-R$_{11}$ is a C$_1$-C$_4$ alkyl.

8. Method for preparing a macromonomer compound of the general formula II wherein n is 1–100; l is 0, $R_1$ is $CH_2=CHCH_2-$ or $CH_2=CH-O-(CH_2)_p$; p is 1–5; m is 1–5; $R_2$ is selected from H; $CH_2=CHCH_2-$, phenyl; $R_3-R_6$ is $C_1-C_4$ alkyl; and W is selected from wherein $R_7-R_{11}$ is a $C_1-C_4$ alkyl, comprising polymerizing a compound of the general formula III with a nitrogen anion IV

9. Method for preparing a macromonomer compound of the general formula II wherein n is 1–100; l is 1, $R_1$ is $CH_2=CHCH_2-$ or $CH_2CH-O-(CH_2)_p$; p is 1–5; m is 1–5; $R_2$ is selected from H; $CH_2=CHCH_2-$ and phenyl; $R_3-R_6$ is $C_1-C_4$ alkyl; and W is selected from comprising polymerizing a nitrogen anion of the general formula IV with a compound selected from (V) and (VI)

wherein $R_7-R_{11}$ is a $C_1-C_4$ alkyl to provide a compound selected from VII and VIII, respectively and polymerizing said VII or VIII with a compound of the general formula III $CH_2=CR_3COOR_4NR_5R_6$.

10. Method for the production of quaternized macromonomers of the general formula I wherein $R_6$ is present, comprising treating said macromonomer wherein $R_6$ is absent with a $R_6$ X quaternizing agent, and wherein the general formula I comprises wherein W is a capping group; l is 0 or 1; n is 1–1000; m is 1–5; $R_1$ is selected from $CH_2=CH-CH_2-$ and $CH_2=CH-O-(CH_2)_p-$, p is 1–5; $R_2$ is selected from H, $C_1-C_4$alkyl, $CH_2=CH-CH_2-$, or phenyl; when $R_1$ is $CH_2=CH-O-(CH_2)_p$, $R_2$ is H or $C_1-C_4$alkyl; and $R_3-R_6$ are $C_1-C_4$ alkyl; and quaternary salts thereof when $R_6$ is $C_1-C_4$alkyl and X is an anion.

11. Method comprising copolymerizing a macromonomer of the general formula I with vinyl monomers to prepare copolymers of general formula X, wherein l is 0 or 1, n is 1–1000, x and y are 10–1000; $R_1$ is $CH_2-CH-O-R_9$ or $CH_2CH-CH_2$, $R_2$ is H or $C_1-C_4$-alkyl; $R_3-R_7$ are $C_1-C_4$ alkyl; and $R_8$ is phenyl or ester, amide groups and wherein the general formula I comprises wherein W is a capping group; l is 0 or 1; n is 1–1000; m is 1–5; $R_1$ is selected from $CH_2=CH-CH_2-$ and $CH_2CH-O-(CH_2)_p-$, p is 1–5; $R_2$ is selected from H, $C_1-C_4$alkyl, $CH_2CH-CH_2-$, or phenyl; when $R_1$ is $CH_2CH-O-(CH_2)_p$, $R_2$ is H or $C_1-C_4$alkyl; and $R_3-R_6$ are $C_1-C_4$ alkyl; and quaternary salts thereof when $R_6$ is $C_1-C_4$alkyl and X is an anion.

12. Method comprising copolymerizing said macromonomer of the general formula I with amphiphilic monomers to prepare water soluble copolymers of general formula XI, wherein l is 1–3, n is 1–1000, x and y are 10–1000; $R_1$ and $R_2$ is $CH_2=CH-CH_2$, $R_3-R_7$ are $C_1-C_4$ alkyl; $R_8$ is methyl; and $R_9$ is an amide group or NHC(O)H or any other hydrophilic groups (XI)

wherein the general formula I comprises (I)

wherein W is a capping group; l is 0 or 1; n is 1–1000; m is 1–5; $R_1$ is selected from $CH_2=CH-CH_2-$ and $CH_2=CH-O-(CH_2)_p-$, p is 1–5; $R_2$ is selected from H, $C_1-C_4$alkyl, $CH_2=CH-CH_2-$, or phenyl; when $R_1$ is $CH_2=CH-O-(CH_2)_p$, $R_2$ is H or $C_1-C_4$alkyl; and $R_3-R_6$ are $C_1-C_4$ alkyl; and quaternary salts thereof when $R_6$ is $C_1-C_4$alkyl and X is an anion.

13. Compound of claim 2 wherein n is 5–200.
14. Compound of claim 3 wherein n is 5–200.
15. Compound of claim 2 wherein n is 10–100.
16. Compound of claim 3 wherein n is 10–100.
17. Compound of claim 2 wherein $R_6$ is $CH_3$.
18. Compound of claim 3 wherein $R_6$ is $CH_3$.
19. Compound of claim 4 wherein $R_6$ is $CH_3$.
20. Compound of claim 5 wherein $R_6$ is $CH_3$.

* * * * *